US012605090B2

(12) United States Patent
Hu et al.

(10) Patent No.: US 12,605,090 B2
(45) Date of Patent: Apr. 21, 2026

(54) GAIT EVALUATING SYSTEM

(71) Applicant: Industrial Technology Research Institute, Hsinchu (TW)

(72) Inventors: Je-Ping Hu, Hsinchu City (TW); Keng-Hsun Lin, Tainan City (TW); Shih-Fang Yang Mao, Hsinchu County (TW); Pin-Chou Li, Hsinchu City (TW); Jian-Hong Wu, Nantou County (TW); Szu-Ju Li, Hsinchu City (TW); Hui-Yu Cho, Taichung City (TW); Yu-Chang Chen, New Taipei City (TW); Yen-Nien Lu, Tainan City (TW); Jyun-Siang Hsu, Taipei City (TW); Nien-Ya Lee, Nantou County (TW); Kuan-Ting Ho, Taipei City (TW); Ming-Chieh Tsai, Hsinchu County (TW); Ching-Yu Huang, Taoyuan City (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 18/919,461

(22) Filed: Oct. 18, 2024

(65) Prior Publication Data
US 2025/0064345 A1 Feb. 27, 2025

Related U.S. Application Data

(63) Continuation-in-part of application No. 17/388,035, filed on Jul. 29, 2021, now abandoned.

(60) Provisional application No. 63/060,607, filed on Aug. 3, 2020.

(51) Int. Cl.
| | |
|---|---|
| *A61B 5/11* | (2006.01) |
| *A61B 5/00* | (2006.01) |
| *A63B 24/00* | (2006.01) |
| *A63B 71/06* | (2006.01) |

(52) U.S. Cl.
CPC ............ *A61B 5/112* (2013.01); *A61B 5/0077* (2013.01); *A61B 5/1128* (2013.01); *A61B 5/6892* (2013.01); *A61B 5/7282* (2013.01); *A63B 24/0075* (2013.01); *A63B 71/0622* (2013.01); *A61B 2562/0247* (2013.01); *A63B 2071/0625* (2013.01)

(58) Field of Classification Search
CPC ...... A61B 5/112; A61B 5/6892; A61B 5/1038
See application file for complete search history.

*Primary Examiner* — Jason M Ip
(74) *Attorney, Agent, or Firm* — JCIPRNET

(57) ABSTRACT

A gait evaluating system including a processor is provided. The processor identifies whether a gait type of the user belongs to a normal gait, a non-neuropathic gait or a neuropathic gait based on step feature values of a user and walking limb feature values of the user. In response to that the gait type of the user belongs to the non-neuropathic gait, the processor controls the display panel to display a first auxiliary information, a second auxiliary information, and a third auxiliary information. The first auxiliary information indicates a potential sarcopenia of the user. The second auxiliary information indicates a dietary guideline for muscle building and muscle strengthening. The third auxiliary information shows a motion instruction video for regaining or maintaining muscle strength of the user.

18 Claims, 8 Drawing Sheets

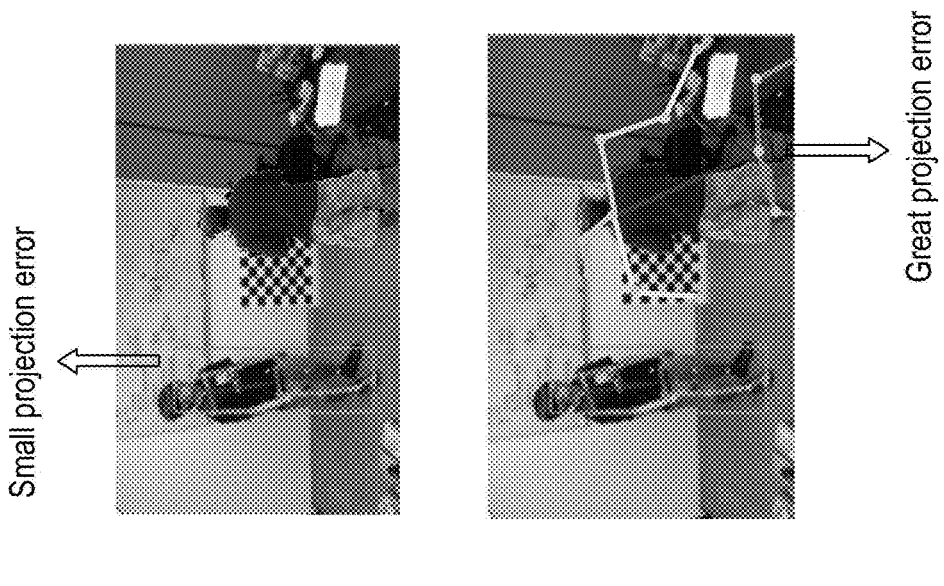
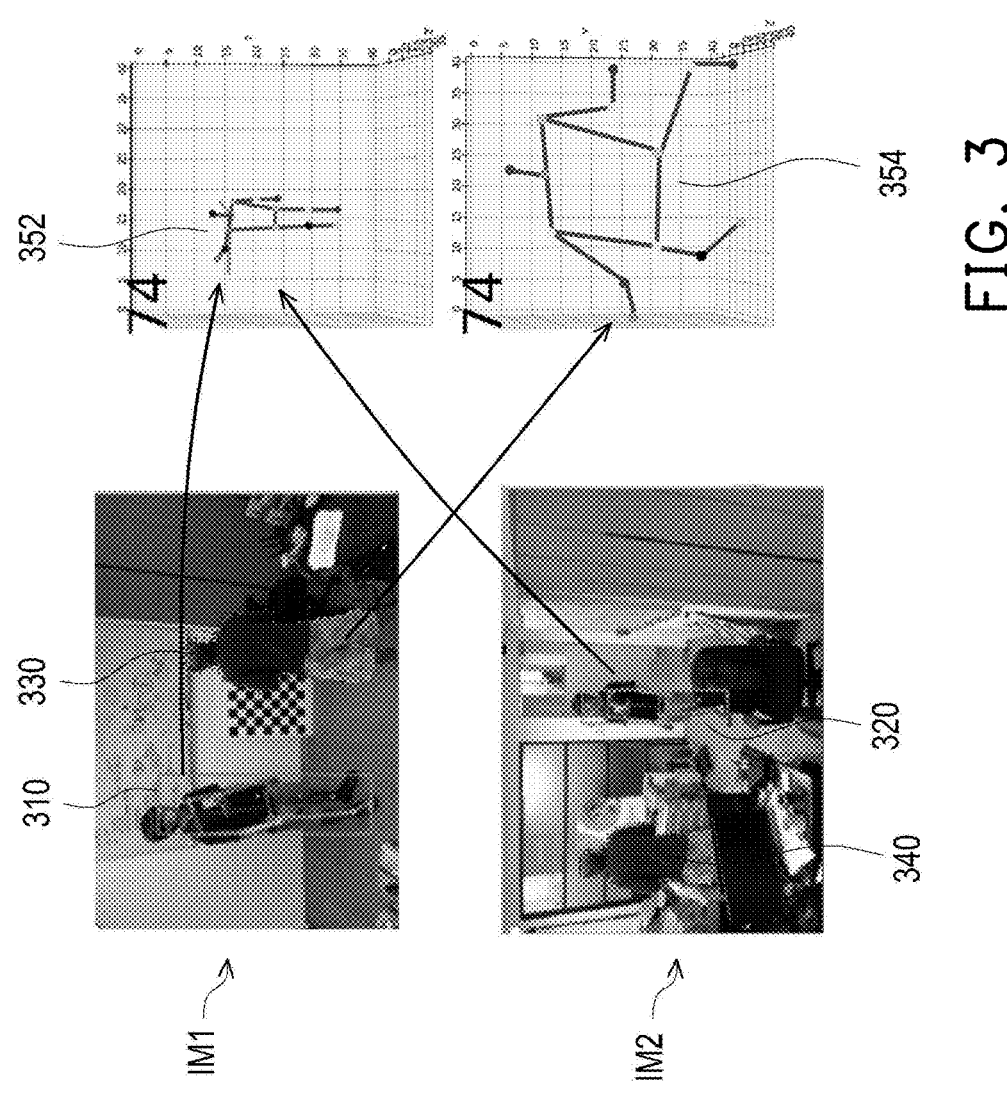
FIG. 3

120

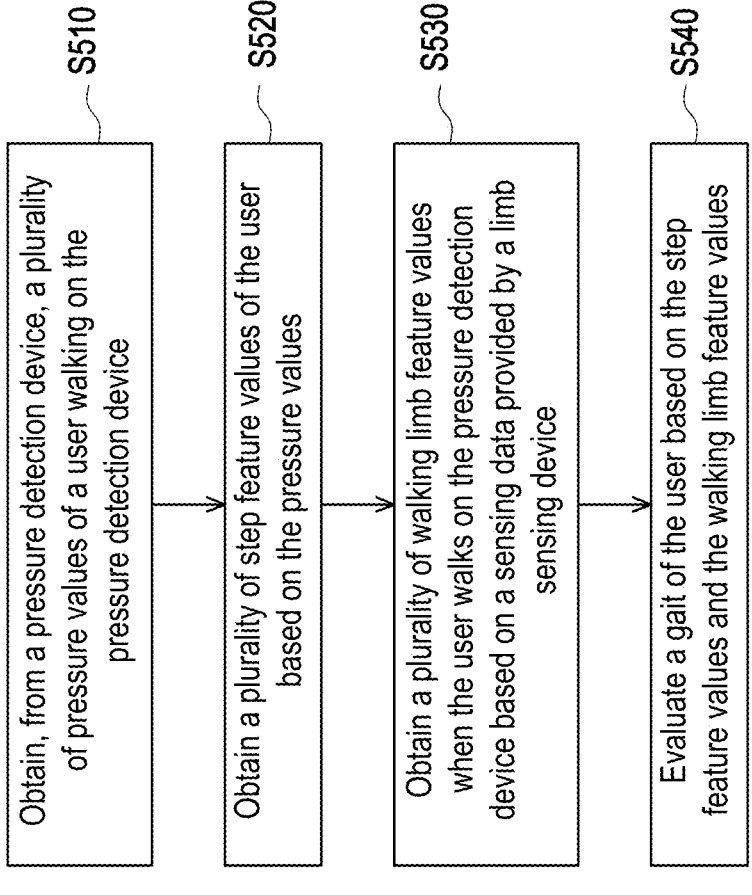

S510

Obtain, from a pressure detection device, a plurality of pressure values of a user walking on the pressure detection device

S520

Obtain a plurality of step feature values of the user based on the pressure values

S530

Obtain a plurality of walking limb feature values when the user walks on the pressure detection device based on a sensing data provided by a limb sensing device

S540

Evaluate a gait of the user based on the step feature values and the walking limb feature values

FIG. 5

GAIT EVALUATING SYSTEM

CROSS-REFERENCE TO RELATED APPLICATION

This application is a continuation-in-part application of and claims the priority benefit of a prior application Ser. No. 17/388,035, filed on Jul. 29, 2021, which claims the priority benefit of U.S. provisional application Ser. No. 63/060,607, filed on Aug. 3, 2020. The entirety of each of the above-mentioned patent applications is hereby incorporated by reference herein and made a part of this specification.

TECHNICAL FIELD

The invention relates to a gait evaluating system, and in particularly to a gait evaluating system which can identify a gait of a user in real time with high accuracy.

BACKGROUND

With trends of decline of birth rate and/or increase of life expectancy, many countries in the world have entered a (super-)aging society. Among the care issues related to the elderly population, how to prevent the elderly population from falls has become one of the important issues.

After research, it is currently known that, gait-related parameters in people's walk may be used to predict future falls. For example, a normalized stride length of certain person may be used to predict the occurrence of repeated fall of the person in the next 6 or 12 months. Besides, people who walk relatively slowly also have a higher mortality rate. In addition, as people age, a forward inclination angle of the torso may also gradually increase. Moreover, for those suffering neurological diseases (e.g., Parkinson's disease, Alzheimer's disease, etc.), the angle of the torso may also be inclined forward or sideways.

Therefore, for those skilled in the art, if a mechanism can be designed where gaits of people can be analyzed to determine whether the gaits of people are normal, it should be able to facilitates grasping the health condition of people, thus achieving the effect of preventing falls.

SUMMARY

In view of the above, the invention provides a gait evaluating system, which may be used to solve the above technical problems.

The invention provides a gait evaluating system. The gait evaluating system includes a pressure detection mat, at least one limb sensor, a display panel, and a processor. The processor is coupled to the pressure detection mat, the at least one limb sensor, and the display panel. The processor is configured to: control the pressure detection mat to detect step pressure values corresponding to a plurality of steps of a user during a time period that the user walks on the pressure detection mat; control the at least one limb sensor to sense limb motions during the same time period that the user walks on the pressure detection mat; generate a plurality of step feature values of the user based on the step pressure values detected by the pressure detection mat; generate a plurality of walking limb feature values based on the limb motions sensed by the at least one limb sensor; and identify whether a gait type of the user belongs to a normal gait, a non-neuropathic gait or a neuropathic gait based on the step feature values and the walking limb feature values. In response to identifying that the gait type of the user belongs to the non-neuropathic gait, the processor is configured to: control the display panel to display a first auxiliary information, and the first auxiliary information indicates a potential sarcopenia of the user; control the display panel to display a second auxiliary information, and the second auxiliary information indicates a dietary guideline for muscle building and for muscle strengthening; and control the display panel to display a third auxiliary information, and the third auxiliary information shows a motion instruction video for regaining or maintaining muscle strength of the user.

BRIEF DESCRIPTION OF THE DRAWINGS

FIG. 3 is a schematic diagram illustrating screening of an integrated skeleton diagram according to the first embodiment of the invention.

FIG. 5 is a flowchart illustrating a gait evaluating method according to an embodiment of the invention.

DESCRIPTION OF THE EMBODIMENTS

Figure 1A:
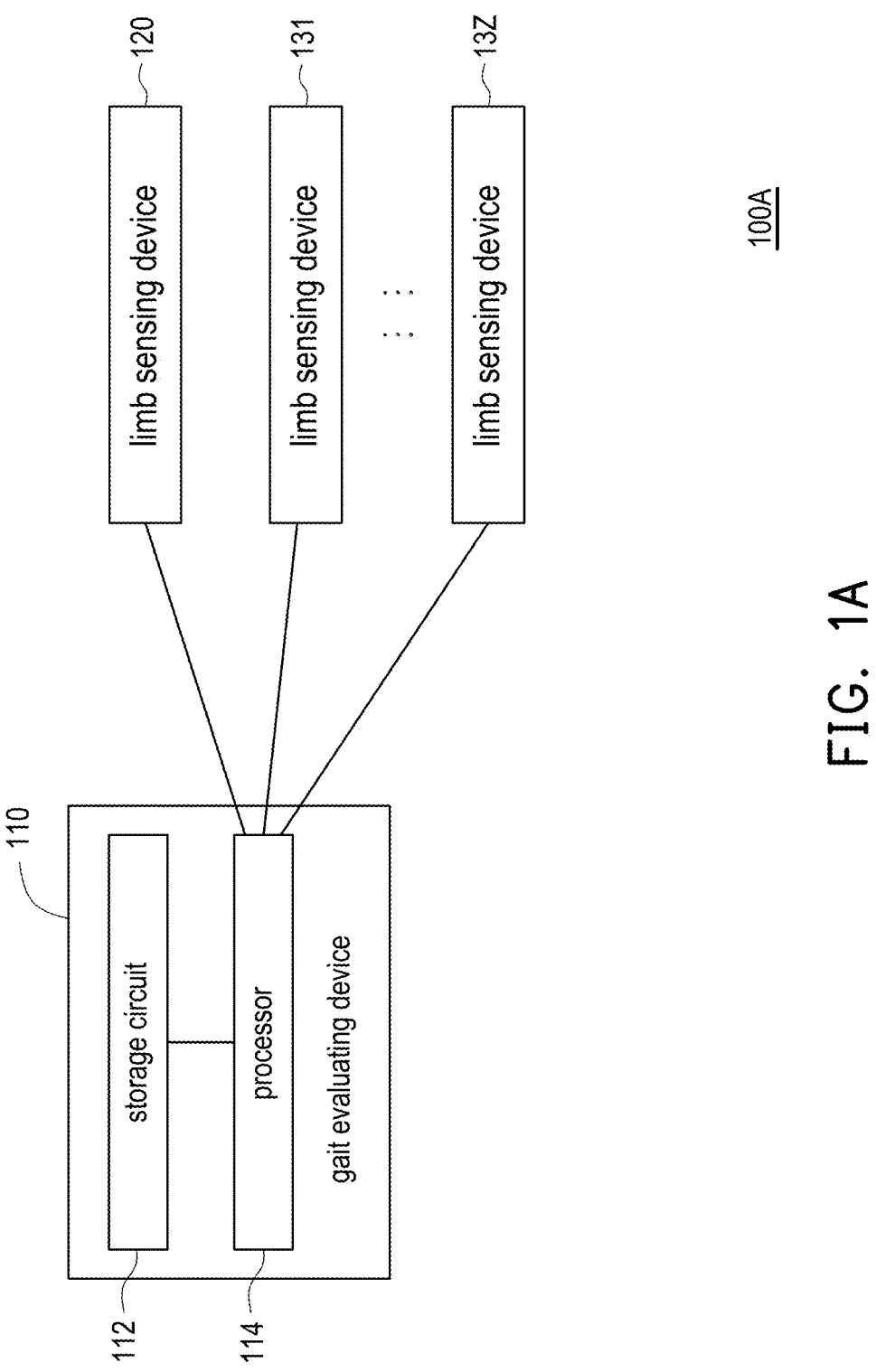
FIG. 1A is a schematic diagram illustrating a gait evaluating system according to an embodiment of the invention.

With reference to FIG. 1A, which is a schematic diagram illustrating a gait evaluating system according to an embodiment of the invention. In FIG. 1A, a gait evaluating system 100A may include a gait evaluating device 110, a pressure detection device 120, and limb sensing devices 131 to 13Z (where Z is a positive integer). According to design requirements, each of the limb sensing devices 131 to 13Z may be a limb sensor. In different embodiments, the gait evaluating device 110 is, for example but not limited to, various computer devices and/or smart devices.

As shown in FIG. 1A, the gait evaluating device 110 may include a storage circuit 112 and a processor 114. The storage circuit 112 is, for example, any form of fixed or mobile random access memory (RAM), read-only memory (ROM), flash memory, hard drives, or other similar devices or a combination of these devices, and may be used to record a plurality of programming codes or modules. In addition, the storage circuit 112 may store a plurality of data generated by the processor 114, the pressure detection device 120, and the limb sensing devices 131 to 13Z.

The processor 114 is coupled to the storage circuit 112, and may be a general purpose processor, a special purpose processor, a conventional processor, a digital signal processor, a plurality of microprocessors, one or more microprocessors combined with a digital signal processor core, a controller, a microcontroller, an application specific integrated circuit (ASIC), a field programmable gate array (FPGA), any other type of integrated circuits, state machines, processors based on the Advanced RISC Machine (ARM), and the like.

In different embodiments, the pressure detection device 120 in FIG. 1A may be embodied as a pressure detection mat including a plurality of pressure detectors, and may also be used for a user (e.g., a person to be performed with gait evaluation) to walk on, to detect a distribution/value of pressure applied to the pressure detection device 120 at each step of the user.

Figure 1B:
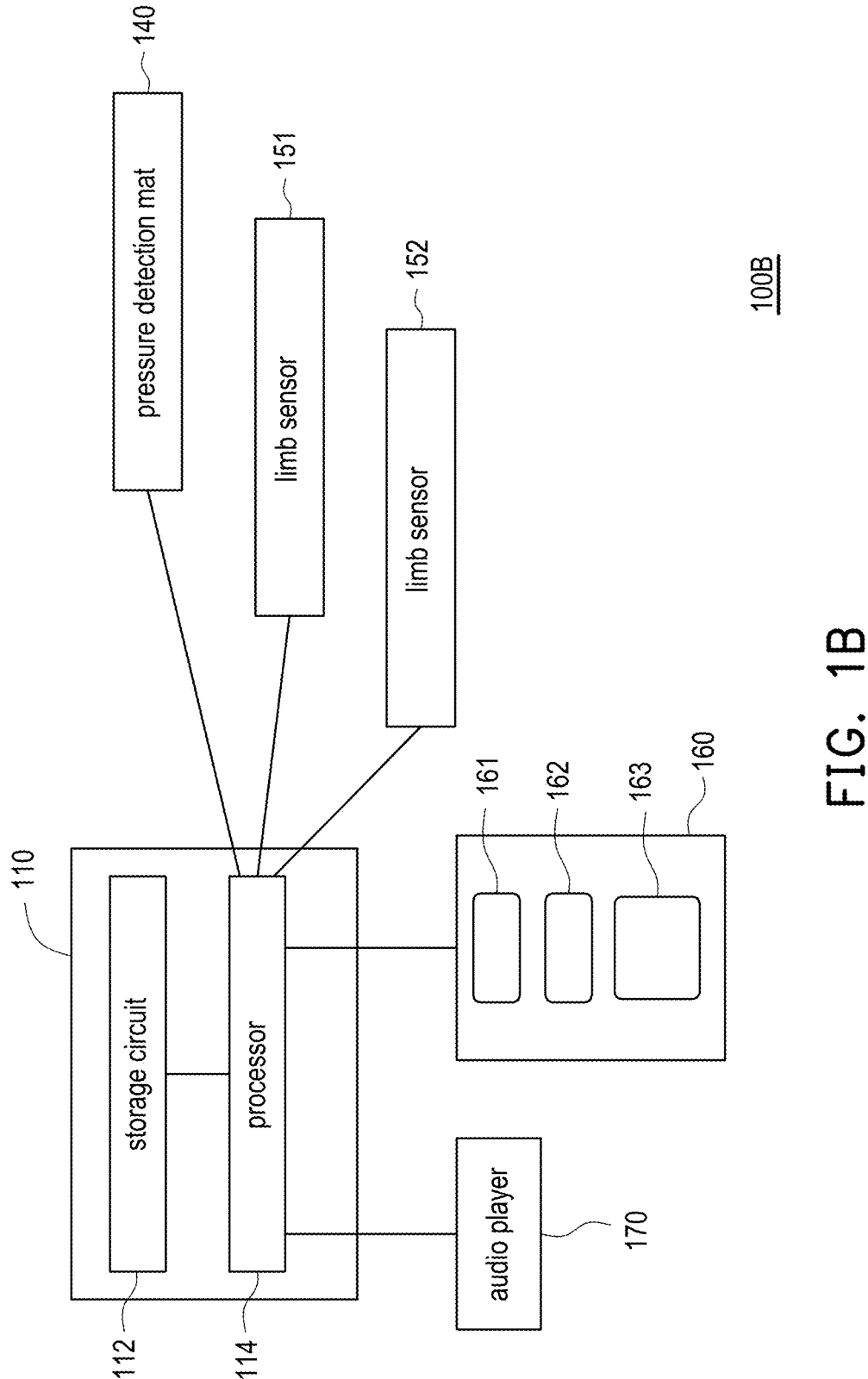
FIG. 1B is a schematic diagram illustrating a gait evaluating system according to another embodiment of the invention.

For example, FIG. 1B is a schematic diagram illustrating a gait evaluating system according to another embodiment of the invention. Referring to FIG. 1B, the gait evaluating system 100B includes a gait evaluating device 110, a pressure detection mat 140, limb sensors 151 and 152, a display panel 160, and an audio player 170. The gait evaluating device 110 includes a storage circuit 112 and a processor 114. The storage circuit 112 may store a plurality of data generated by the processor 114, the pressure detection mat 140, and the limb sensors 151 and 152. The processor 114 is coupled to the pressure detection mat 140, the limb sensors 151 and 152, the display panel 160, and the audio player 170. The processor 114 may control the pressure detection mat 140 to detect step pressure values corresponding to a plurality of steps of a user during a time period that the user walks on the pressure detection mat 140. Then, the processor 114 may generate a plurality of step feature values of the user based on the step pressure values detected by the pressure detection mat 140.

In the embodiment of FIG. 1B, only two limb sensors 151 and 152 are coupled to the processor 114. In other embodiments, more than two limb sensors may be coupled to the processor 114. The processor 114 may control the limb sensors 151 and 152 to sense limb motions during the same time period that the user walks on the pressure detection mat 140. For example, each of the limb sensors 151 and 152 may be a video camera to capture a walking image of the user walking on the pressure detection mat 140. Then, the processor 114 may generate a plurality of walking limb feature values based on the limb motions sensed by the limb sensors 151 and 152.

In FIG. 1B, the processor 114 may identify whether a gait type of the user belongs to a normal gait or an abnormal gait (i.e., a non-neuropathic gait and a neuropathic gait) based on the step feature values and the walking limb feature values. When the processor 114 identifies that the gait of the user belongs to the abnormal gait, the processor 114 may provide a corresponding enablement suggestion.

For example, if the gait of the user belongs to a non-neuropathic gait (e.g., gait abnormality resulting from sarcopenia, bow legs, knock knees, or the like), the processor 114 may provide a strength training suggestion corresponding to the non-neuropathic gait as the enablement suggestion. In an embodiment, the strength training suggestion may base its content on the relevant literature documents of physical therapy (e.g., literature documents of strength training for treatment of bow legs or knock knees). Nonetheless, the disclosure is not limited thereto.

Specifically, when the processor 114 identifies that the gait type of the user belongs to the non-neuropathic gait resulting from sarcopenia, the processor 114 may control the display panel 160 to display a first auxiliary information 161. The first auxiliary information 161 may indicate the potential sarcopenia of the user. Then, the processor 114 may control the display panel 160 to display a second auxiliary information 162 and a third auxiliary information 163. The second auxiliary information 162 may indicate a dietary guideline for muscle building and for muscle strengthening. The third auxiliary information 163 may show a motion instruction video, so that the user may know how to regain or maintain muscle strength from the motion instruction video.

In addition, if the gait of the user belongs to a neuropathic gait (e.g., gait abnormality caused by Parkinson's disease or Alzheimer's disease), then the processor 114 may provide a rhythmic gait training suggestion corresponding to the neuropathic gait as the enablement suggestion. For example, when the processor 114 identifies that the gait type of the user belongs to the neuropathic gait caused by Parkinson's disease, the processor 114 may control the audio player 170 to output a rhythmic audio. The rhythmic audio may facilitate the user with an improved cadence and an improved gait speed.

Therefore, after the user taking a small amount of walk on the pressure detection mat 140, the processor 114 in FIG. 1B can quickly identify a gait of the user from a normal gait, a non-neuropathic gait, and a neuropathic gait, and the processor 114 may provide a corresponding enablement suggestion. Accordingly, the gait evaluating system 100B can reduce fall risk likelihood of the user.

Figure 2A:
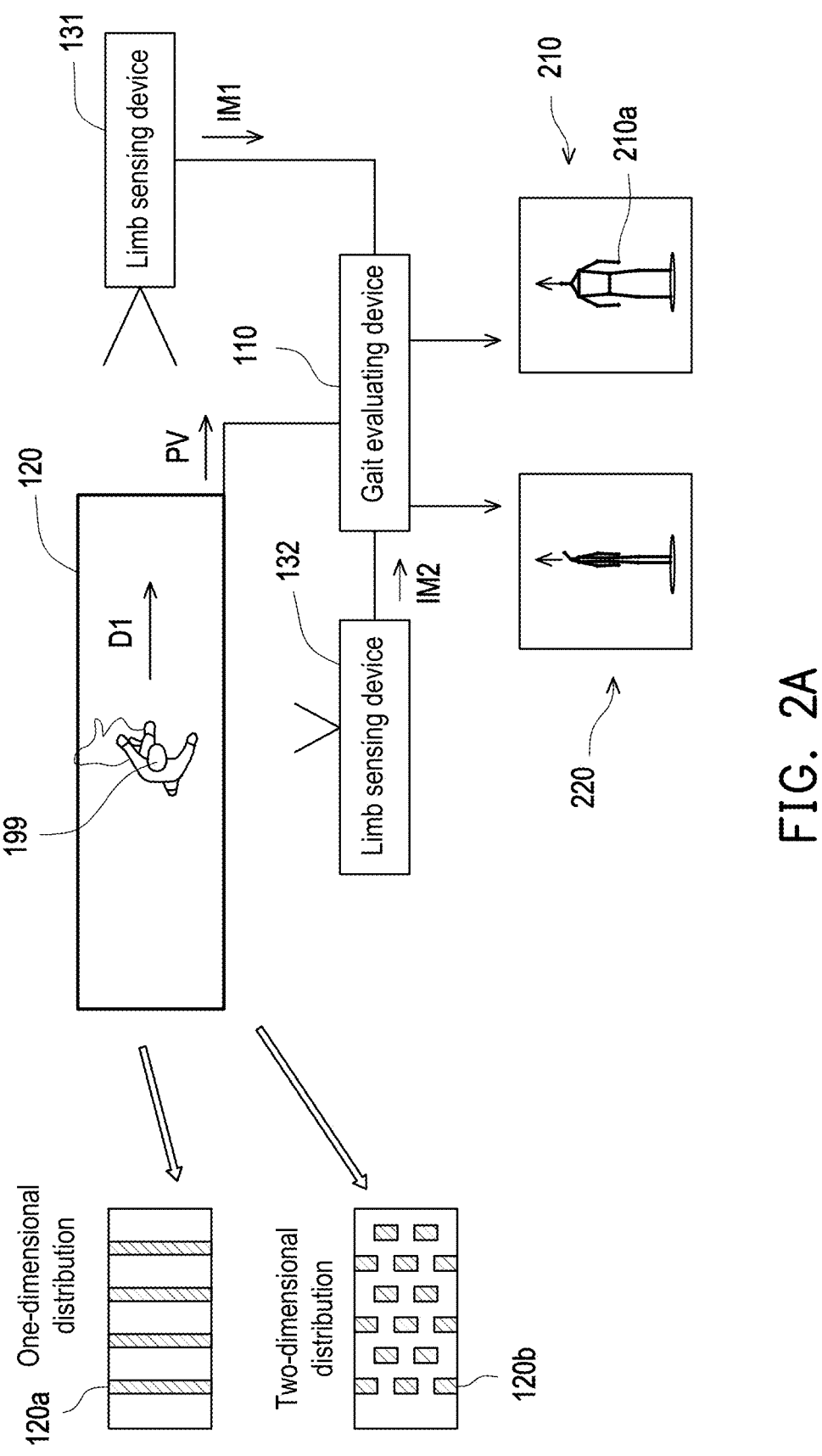
FIG. 2A is a schematic diagram illustrating a gait evaluating system according to a first embodiment of the invention.

FIG. 2A is a schematic diagram illustrating a gait evaluating system according to a first embodiment of the invention. In FIG. 2A, the pressure detection device 120 may be embodied as a pressure detection mat, and a user 199 may walk on the pressure detection device 120 in a walking direction D1 upon request.

In an embodiment, the pressure detection device 120 may include a plurality of pressure detectors 120a exhibiting a one-dimensional distribution. In another embodiment, the pressure detection device 120 may also include a plurality of pressure detectors 120b exhibiting a two-dimensional distribution. Nonetheless, the disclosure is not limited thereto. In some embodiments, the length of the pressure detection mat may be greater than or equal to 3 meters, and the width may be greater than or equal to 0.4 meters. Besides, in some embodiments, the pressure detection mat may be provided with one pressure detector 120a (or one pressure detector 120b) per 50 cm$^2$ (or less). In some embodiments, the pressure detection mat may also be provided with one pressure detector 120a (or one pressure detector 120b) per 6.25 cm$^2$, but it is not limited thereto.

In the first embodiment, when the user 199 walks on the pressure detection device 120, the pressure detectors distributed on the pressure detection device 120 may detect a plurality of step pressure values PV corresponding to steps of the user 199. The pressure detection device 120 may provide the step pressure values PV to the gait evaluating device 110 for further analysis by the gait evaluating device 110.

Referring to FIG. 1A, the limb sensing devices 131 to 13Z may each be embodied as a video camera to capture a walking image of the user walking on the pressure detection device 120.

For example, the limb sensing devices 131 and 132 in FIG. 2A may be respectively embodied as a first video camera and a second video camera. The first video camera may be used to capture a first walking image IM1 when the user 199 walks on the pressure detection device 120, and the second video camera may be used to capture a second walking image IM2 when the user 199 walks on the pressure detection device 120.

As shown in FIG. 2A, the imaging direction of the limb sensing device 131 (i.e., the first video camera) may be opposite to the walking direction D1 of the user 199, to thereby capture a front image of the user 199 when walking. In addition, the imaging direction of the limb sensing device 132 (i.e., the second video camera) may be perpendicular to the walking direction D1 of the user 199, to thereby capture a side image (e.g., from the right side) of the user 199 when walking.

In the first embodiment, for the first walking image IM1 and the second walking image IM2 obtained by the first video camera and the second video camera at a t-th time point (where t is a time index value), the gait evaluating device 110 may obtain a first skeleton diagram 210 and a second skeleton diagram 220 respectively in the first walking image IM1 and the second walking image IM2. In the embodiment of the invention, the gait evaluating device 110 may obtain the first skeleton diagram 210 and the second skeleton diagram 220 respectively in the first walking image IM1 and the second walking image IM2 based on any known image processing algorithms, for example but not limited to, the literature document "Z. Cao, G. Hidalgo, T. Simon, S. -E. Wei and Y. Sheikh, OpenPose: Realtime Multi-Person 2D Pose Estimation Using Part Affinity Fields, in IEEE Transactions on Pattern Analysis and Machine Intelligence, vol. 43, no. 1, pp. 172-186, 1 Jan. 2021".

In the first embodiment, the first skeleton diagram 210 and the second skeleton diagram 220 may, for example, correspond to the human body posture of the user 199 at the t-th time point, and may each include a plurality of reference points corresponding to a plurality of joints of the user 199 (e.g., corresponds to a reference point 210a at a wrist of the user 199).

In an embodiment, the gait evaluating device 110 may project the first skeleton diagram 210 and the second skeleton diagram 220 into a first integrated skeleton diagram based on the relative position between the first video camera and the second video camera. For related projection technology, reference may be made to the literature document "Z. Cao, G. Hidalgo, T. Simon, S. -E. Wei and Y. Sheikh, OpenPose: Realtime Multi-Person 2D Pose Estimation Using Part Affinity Fields, in IEEE Transactions on Pattern Analysis and Machine Intelligence, vol. 43, no. 1, pp. 172-186, 1 Jan. 2021".

In an embodiment, the first integrated skeleton diagram may include a plurality of joint angles (e.g., neck angle, shoulder angle, elbow angle, wrist angle, hip angle, knee angle, ankle angle, etc.) at the t-th time point. The joint angles correspond to the joints (e.g., neck, shoulders, elbows, wrists, hips, knees, ankles, etc.) of the user 199. After that, the gait evaluating device 110 may obtain a plurality of angle values of the joint angles, and take the angle values as a plurality of walking limb feature values of the user 199 at the t-th time point.

In some embodiments, after obtaining the first skeleton diagram 210, the second skeleton diagram 220, and/or the first integrated skeleton diagram, the gait evaluating device 110 may, for example, remove outliers from the skeleton diagrams based on the median filter or other similar noise reduction technology, and then remove high-frequency fluctuations from the skeleton diagrams through a fast Fourier transform (FFT). After that, the gait evaluating device 110 may also smooth the movement between the skeleton diagrams at different time points through poly-fitting. Nonetheless, the disclosure is not limited thereto.

Figure 2B:
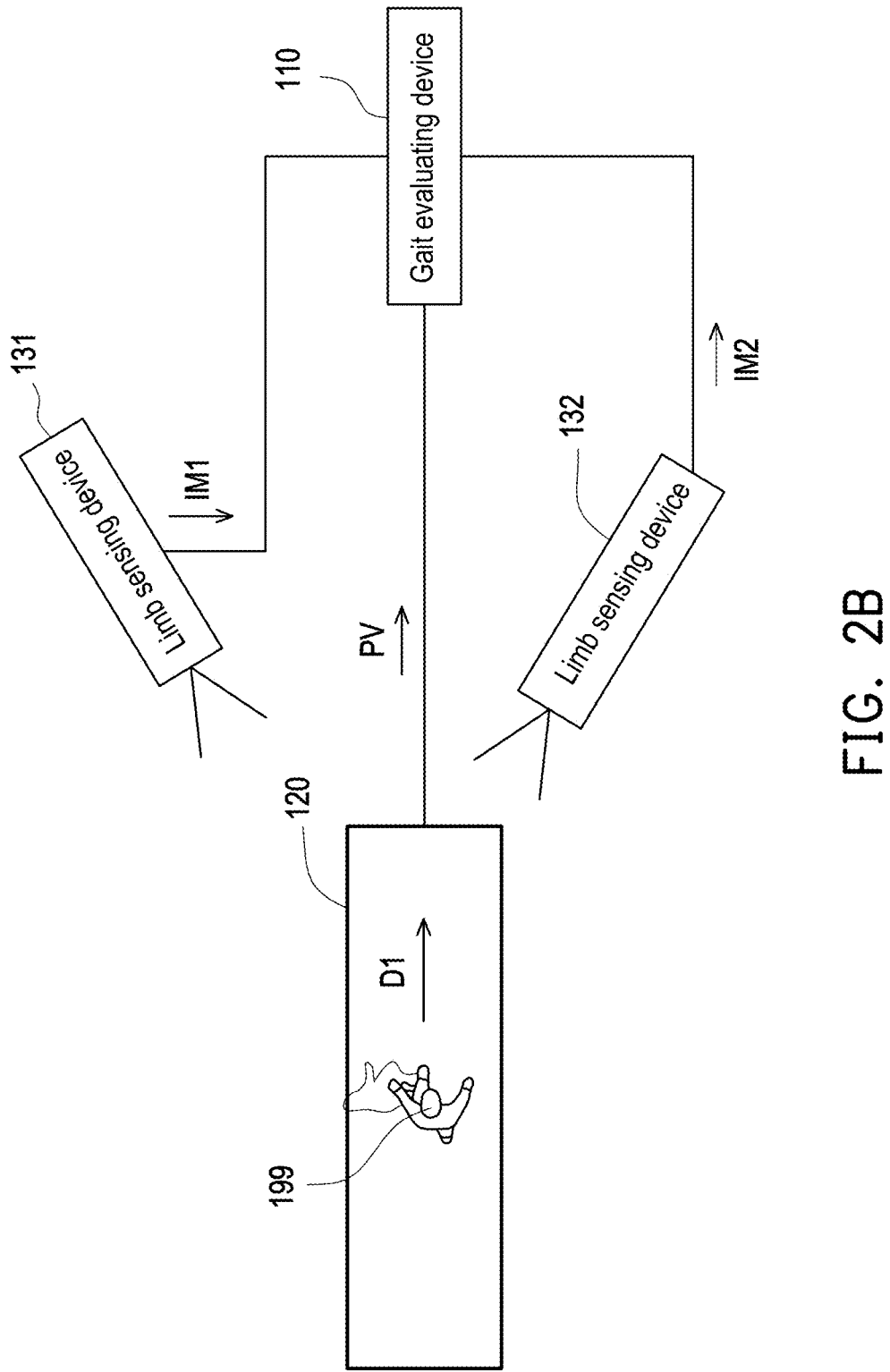
FIG. 2B is a schematic diagram illustrating another gait evaluating system according to FIG. 2A.

With reference to FIG. 2B, which is a schematic diagram illustrating another gait evaluating system according to FIG. 2A. In FIG. 2B, except that the imaging directions of the limb sensing devices 131 and 132 are different from those of FIG. 2A, the rest of the configuration is generally the same as that of FIG. 2A.

Specifically, in FIG. 2B, from two sides in front of the user 199, the limb sensing device 131 (i.e., the first video camera) and the limb sensing device 132 (i.e., the second video camera) may respectively capture the first walking image IM1 and the second walking image IM2 of the user 199 when the user 199 walks on the pressure detection device 120 along the walking direction D1. After that, the gait evaluating device 110 may also obtain the first skeleton diagram 210 and the second skeleton diagram 220 respectively from the first walking image IM1 and the second walking image IM2, and project the first skeleton diagram 210 and the second skeleton diagram 220 into the first integrated skeleton diagram based on the aforementioned teaching.

In an embodiment, when human bodies other than that of the user 199 are present in the first walking image IM1 and the second walking image IM2, the gait evaluating device 110 may thus be unable to correctly obtain the integrated skeleton diagram corresponding to the user 199. Therefore, in the embodiments of the invention, human bodies other than that of the user 199 may be excluded through a specific mechanism, thereby increasing the gait evaluation accuracy.

In an embodiment, after obtaining the first integrated skeleton diagram, the gait evaluating device 110 may further determine whether the first integrated skeleton diagram satisfies a specified condition. If so, the gait evaluating device 110 may then obtain the angle values of the joint angles, and take the angle values as the walking limb feature values of the user 199 at the t-th time point.

In an embodiment, the gait evaluating device 110 may determine whether the first walking image IM1 and the second walking image IM2 do not include skeleton diagrams corresponding to other human bodies. If so, this means that the first skeleton diagram 210 and the second skeleton diagram 220 correspond to the human body (i.e., the user 199) to be performed with gait evaluation at present. Therefore, the gait evaluating device 110 may correspondingly determine that the first integrated skeleton diagram satisfies the specified condition. If not, this means that skeleton diagrams corresponding to other human bodies are present in the first walking image IM1 and the second walking image IM2. Therefore, the gait evaluating device 110 may perform further screening to find the integrated skeleton diagram actually corresponding to the user 199. The related details accompanied with FIG. 3 will be further described.

With reference to FIG. 3, which is a schematic diagram illustrating screening of an integrated skeleton diagram according to the first embodiment of the invention. In this embodiment, it is assumed that the first walking image IM1 and the second walking image IM2 obtained at the t-th time point are as shown in FIG. 3.

From FIG. 3, it can be seen that the first walking image IM1 includes a first skeleton diagram 310 and a third skeleton diagram 330, and the second walking image IM2 includes a second skeleton diagram 320 and a fourth skeleton diagram 340. The first skeleton diagram 310 and the second skeleton diagram 320 correspond to the user to be performed with gait evaluation at present, and the third skeleton diagram 330 and the fourth skeleton diagram 340 correspond to another human body.

In this case, the gait evaluating device 110 may project the first skeleton diagram 310 and the second skeleton diagram 320 into a first integrated skeleton diagram 352, and project the third skeleton diagram 330 and the fourth skeleton diagram 340 into a second integrated skeleton diagram 354.

Then, the gait evaluating device 110 may obtain a first projection error of the first integrated skeleton diagram 352 and a second projection error of the second integrated skeleton diagram 354, and determine whether the first projection error is less than the second projection error.

In the scenario of FIG. 3, assuming that the first projection error is determined to be less than the second projection error, the gait evaluating device 110 may determine that the first integrated skeleton diagram 352 satisfies the specified condition, and may obtain the angle values of the joint angles in the first integrated skeleton diagram 352. After that, the gait evaluating device 110 may then take the angle values as the walking limb feature values of the user 199 at the t-th time point.

In other embodiments, in response to determining that the first projection error is not less than the second projection error, this means that the first integrated skeleton diagram 352 does not correspond to the human body to be performed with gait evaluation. Therefore, the gait evaluating device 110 may determine that the first integrated skeleton diagram 352 does not satisfy the specified condition. After that, the gait evaluating device 110 may obtain the walking limb feature values of the user 199 at the t-th time point based on the second integrated skeleton diagram 354.

Accordingly, even in a case where the gait evaluating system 100A (or the gait evaluating system 100B) is disposed in a general field not dedicated to gait detection, in the embodiments of the invention, the target to be performed with gait evaluation may still be evaluated after other irrelevant human bodies are excluded. Accordingly, an effect that the target may be evaluated without noticing that the target is being evaluated can be achieved.

In other embodiments, FIG. 2A and FIG. 2B may also include more video cameras to capture images of the user 199 from different angles. In this case, the gait evaluating device 110 may correspondingly obtain a more accurate integrated skeleton diagram, but it is not limited thereto.

Figure 4:
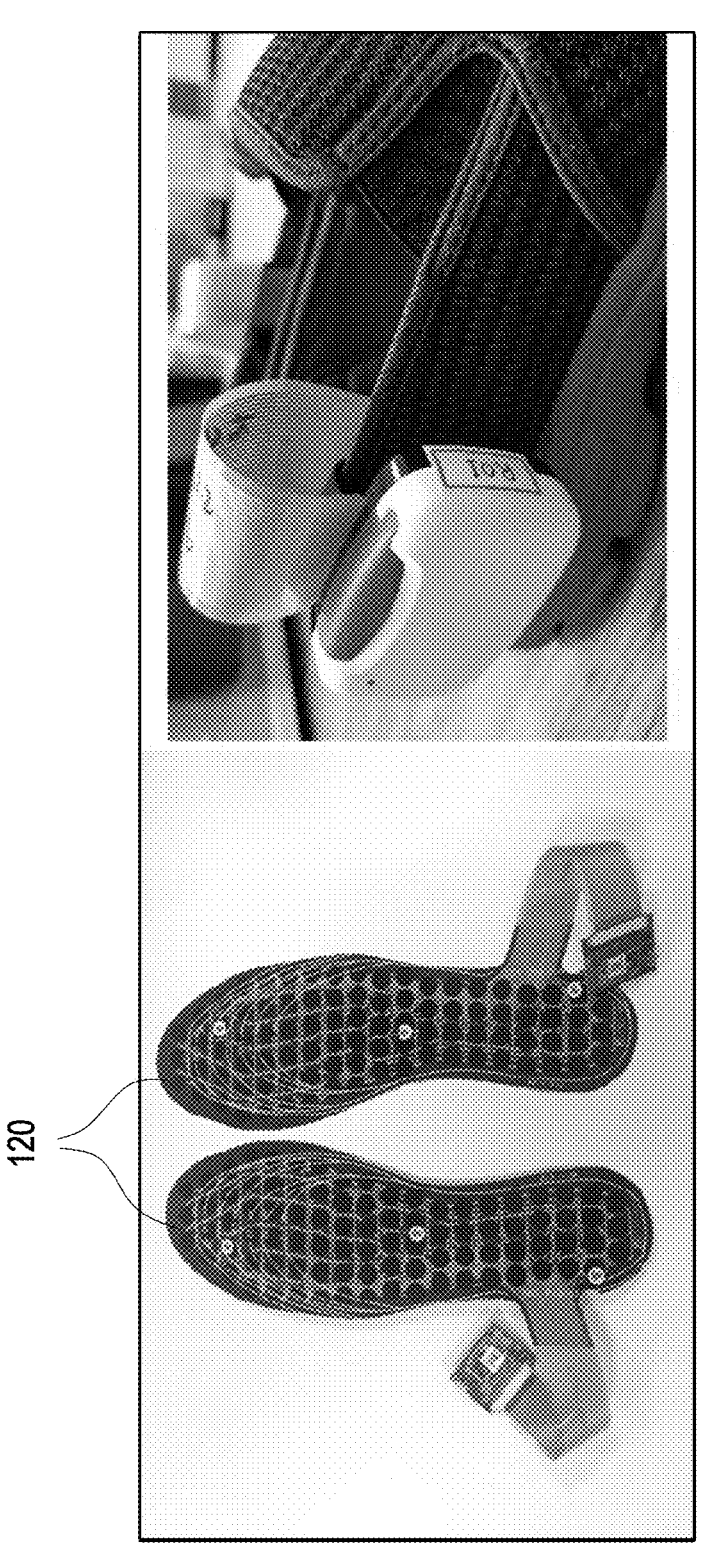
FIG. 4 is a schematic diagram illustrating a pressure detection device according to a second embodiment of the invention.

With reference to FIG. 4, which is a schematic diagram illustrating a pressure detection device according to a second embodiment of the invention. In FIG. 4, the pressure detection device 120 may be embodied as a pressure detection insole including a plurality of pressure detectors. In an embodiment, the pressure detection device 120 may be disposed in the shoes of the user 199 for the user 199 to wear and walk in. In this case, the pressure detection insole may detect the pressure value PV of each step of the user 199 when the user 199 walks, and may provide the pressure value PV corresponding to each step to the gait evaluating device 110. In the second embodiment, for the relevant measurement means, reference may be made to the content of the literature document "S. J. M. Bamberg, A. Y. Benbasat, D. M. Scarborough, D. E. Krebs and J. A. Paradiso, "Gait Analysis Using a Shoe-Integrated Wireless Sensor System," in *IEEE Transactions on Information Technology in Biomedicine*, vol. 12, no. 4, pp. 413-423, July 2008", which will not be repeatedly described herein.

In a third embodiment, the limb sensing devices 131 to 13Z may also be embodied as a plurality of dynamic capturing elements (e.g., inertial measurement units) that may be worn on the user 199. The dynamic capturing elements may be distributed at the joints (e.g., neck, shoulders, elbows, wrists, hips, knees, ankles, etc.) of the user 199 to capture movements of the joints.

For example, the gait evaluating device 110 may obtain, at the t-th time point, a plurality of three-dimensional spatial positions of the dynamic capturing elements, and accordingly establish a spatial distribution diagram of the dynamic capturing elements at the t-th time point. The spatial distribution diagram at the t-th time point may include a plurality of reference points corresponding to the dynamic capturing elements.

After that, according to the relative position between the joints of the user 199, the gait evaluating device 110 may connect the reference points in the spatial distribution diagram into the skeleton diagram (which may have an aspect similar to that of the first integrated skeleton diagram 352 of FIG. 3) of the user 199 at the t-th time point. The skeleton diagram may include the joint angles of the joints at the t-th time point. Then, the gait evaluating device 110 may obtain the angle values of the joint angles, and take the angle values as the walking limb feature values of the user 199 at the t-th time point.

In the third embodiment, for the details of detection through the dynamic capturing elements, reference may be made to the content of the literature documents "Schlachetzki J C M, Barth J, Marxreiter F, Gossler J, Kohl Z, Reinfelder S, Gassner H, Aminian K, Eskofier B M, Winkler J, Klucken J. Wearable sensors objectively measure gait parameters in Parkinson's disease. PLoS One. 2017 Oct. 11" and "Qilong Yuan, I. Chen and Ang Wei Sin, "Method to calibrate the skeleton model using orientation sensors," 2013 IEEE International Conference on Robotics and Automation, 2013", which will not be repeatedly described herein.

In an embodiment, each joint of the user 199 may be predetermined with a corresponding angle range of motion. After obtaining the skeleton diagram of the user 199 at the t-th time point, the gait evaluating device 110 may determine whether the angle value of any joint angle in the skeleton diagram does not fall within the corresponding angle range of motion. If so, this means that the current skeleton diagram may contain a detection error, so the gait evaluating device 110 may correspondingly discard the skeleton diagram at the t-th time point.

For example, assuming that the angle range of motion corresponding to the elbow joint is 30 degrees to 180 degrees. In this case, if the gait evaluating device 110 determines that the joint angle of the elbow in the skeleton diagram at the t-th time point is less than 30 degrees or greater than 180 degrees, the gait evaluating device 110 may correspondingly discard the skeleton diagram at the t-th time point, but it is not limited thereto.

In the embodiments of the invention, the processor 114 may access the modules and programming codes recorded in the storage circuit 112 to realize the gait evaluating method provided by the invention, which will be described in detail as follows.

With reference to FIG. 5, which is a flowchart illustrating a gait evaluating method according to an embodiment of the invention. The method of the embodiment may be performed by the gait evaluating system 100A of FIG. 1A. Each of steps of FIG. 5 accompanied with the elements shown in FIG. 1 will be described in detail below.

First, in step S510, the processor 114 may obtain, from the pressure detection device 120, a plurality of step pressure values PV of the user 199 walking on the pressure detection device 120. In different embodiments, the processor 114 may obtain the step pressure values PV with reference to the description in the above embodiments, which will not be repeated herein.

In step S520, the processor 114 may obtain a plurality of step feature values of the user 199 based on the step pressure values PV. In different embodiments, based on the step pressure values PV, the processor 114 may obtain at least one of a gait speed, a step length, a stride length, a cadence, a step width, a gait cycle, a stance time, a swing time, a center of pressure, a moving trajectory, a double support time, and a foot pressure distribution of the user 199 as the step feature values.

In some embodiments, the processor 114 may also obtain a stride-to-stride variation of the user 199 based on the step pressure values PV. The stride-to-stride variation may include, but is not limited to, at least one of a swing time variation, a double support time variation, a step length time variation, and a stride length time variation.

In some embodiments, the user 199 may perform a timed up and go test (TUG) on the pressure detection device 120 upon request. In this case, based on the step pressure values PV, the processor 114 may also obtain at least one of a get-up time, a turn time, a sit-down time, a walk speed, a walk time, and a total performance time of the user 199 in the timed up and go test as part of the step feature values. Nonetheless, the disclosure is not limited thereto.

Figure 6:
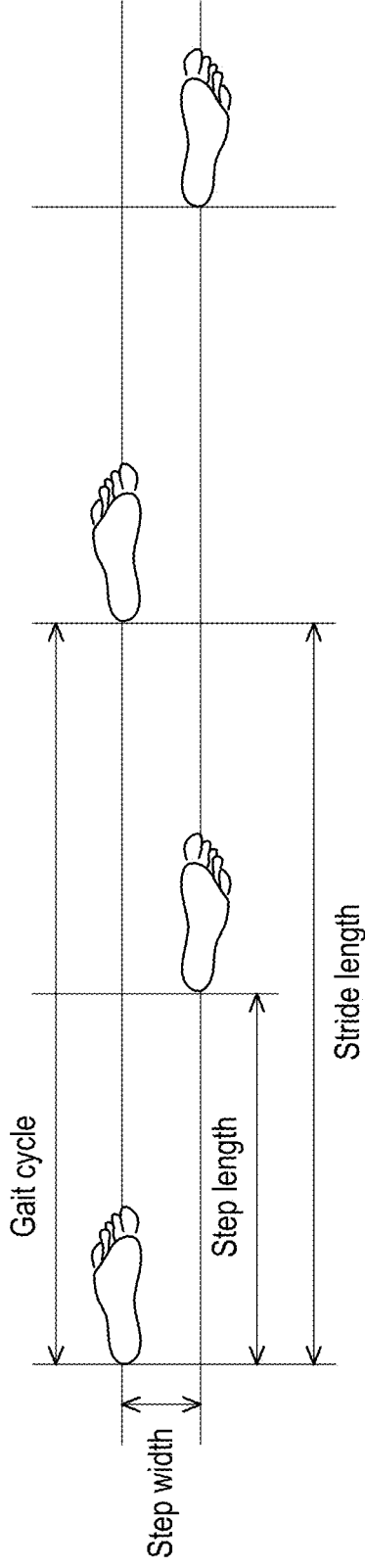
FIG. 6 is a schematic diagram illustrating a plurality of step feature values according to an embodiment of the invention.

With reference to FIG. 6, which is a schematic diagram illustrating a plurality of step feature values according to an embodiment of the invention. FIG. 6 illustrates the difference between the terms such as step length, stride length, step width, and the like. For further details of the step feature values, reference may be made to the literature documents "Pirker W, Katzenschlager R. Gait disorders in adults and the elderly: A clinical guide. Wien Klin Wochenschr. 2017; 129 (3-4):81-95. doi: 10.1007/s00508-016-1096-4" and "Bohannon R W, Williams Andrews A. Normal walking speed: a descriptive meta-analysis. Physiotherapy. 2011", which will not be repeatedly described herein.

Besides, for the details of obtaining the step feature values based on the step pressure values PV, reference may be made to the literature documents "Yoo S D, Kim H S, Lee J H, Yun D H, Kim D H, Chon J, Lee S A, Han Y J, Soh Y S, Kim Y, Han S, Lee W, Han Y R. Biomechanical Parameters in Plantar Fasciitis Measured by Gait Analysis System With Pressure Sensor. Ann Rehabil Med. 2017 December" and "Greene B R, O'Donovan A, Romero-Ortuno R, Cogan L, Scanaill C N, Kenny R A. Quantitative falls risk assessment using the timed up and go test. IEEE Trans Biomed Eng. 2010 December", which will not be repeatedly described herein.

In step S530, based on sensing data provided by the limb sensing devices 131 to 13Z, the processor 114 may obtain a plurality of walking limb feature values when the user 199 walks on the pressure detection device. In different embodiments, the processor 114 may obtain the walking limb feature values (e.g., a plurality of angle values of a plurality of joint angles of the user 199) based on the sensing data (e.g., the first walking image IM1 and the second walking image IM2) provided by the limb sensing devices 131 to 13Z with reference to the description in the above embodiments, which will not be repeated herein.

Then, in step S540, the processor 114 may evaluate a gait of the user 199 based on the step feature values and the walking limb feature values. In different embodiments, the processor 114 may evaluate the gait of the user 199 based on different ways, which will be further described below.

In a fourth embodiment, the processor 114 may determine whether the step feature values and the walking limb feature values of the user 199 do not satisfy a corresponding first statistical standard. In response to determining that Y of the step feature values and the walking limb feature values of the user 199 (where Y is a specified number) does not satisfy the corresponding first statistical standard, the processor 114 may determine that the gait of the user 199 belongs to an abnormal gait, and in the opposite case, the processor 114 may determine that the gait of the user 199 belongs to a normal gait.

In different embodiments, the first statistical standard corresponding to the step feature values and the walking limb feature values may be determined in different ways.

For example, an average gait speed of males in the sixties is statistically 1.34 m/s. Accordingly, when the user 199 is a male between 60 and 69 years old, the first statistical standard corresponding to the gait speed may be set to 1.34 m/s. Besides, since an average gait speed of healthy elder people is statistically 1.1 m/s to 1.5 m/s, when the user 199 is an elder person, the first statistical standard corresponding to the gait speed may be set to 1.Lm/s. Nonetheless, the disclosure is not limited thereto.

In an embodiment, the normal stride length of ordinary people is about 76 to 92 cm on average, so the first statistical standard corresponding to the stride length of the user 199 may be set to 76 cm. Nonetheless, the disclosure is not limited thereto.

Based on a similar concept to the above teaching, the processor 114 may also correspondingly determine the first statistical standard corresponding to the step feature values and the walking limb feature values, for example, the cadence, a TUG time, a torso inclination angle, the stride-to-stride variation, a heel strike angle, and a toe-off angle based on the relevant literature documents/statistical data (e.g., the content of "Gong H, Sun L, Yang R, Pang J, Chen B, Qi R, Gu X, Zhang Y, Zhang T M. Changes of upright body posture in the sagittal plane of men and women occurring with aging—a cross sectional study. BMC Geriatr. 2019 Mar. 5", "Oeda T, Umemura A, Tomita S, Hayashi R, Kohsaka M, Sawada H. Clinical factors associated with abnormal postures in Parkinson's disease. PLoS One. 2013 Sep. 19", and "Schlachetzki J C M, Barth J, Marxreiter F, Gossler J, Kohl Z, Reinfelder S, Gassner H, Aminian K, Eskofier B M, Winkler J, Klucken J. Wearable sensors objectively measure gait parameters in Parkinson's disease. PLoS One. 2017 Oct. 11").

For example, the first statistical standard corresponding to the cadence may be 1.2 times/s, and the first statistical standard corresponding to the TUG time may be less than 20 seconds. In addition, the first statistical standard of the torso inclination angle is, for example, that a square root of the sum of squares of the total inclination angles toward the front and back/the left and right must be less than 10 degrees. The first statistical standard of the stride-to-stride variation is, for example, that the step length time variation must be less than 4%, the swing time variation must be less than 5%, the double support time variation must be less than 8%, the stride length time variation must be less than 4%, and the like. Nonetheless, the disclosure is not limited thereto.

Besides, the first statistical standard of the heel strike angle, for example, must be greater than 20 degrees, and the first statistical standard of the toe-off angle, for example, must be greater than 55 degrees. Nonetheless, the disclosure is not limited thereto.

In an embodiment, when the user 199 belongs to a specific group including a plurality of group members, the processor 114 may also determine the first statistical standard corresponding to each step feature value and each walking limb feature value based on the properties of the specific group.

For example, the processor 114 may obtain a plurality of reference step feature values and a plurality of reference walking limb feature values of the group members of the specific group, and accordingly estimate the first statistical standard of each of the step feature values and each of the walking limb feature values. In some embodiments, the reference step feature values and the reference walking limb feature values of each group member may correspond to the step feature values and the walking limb feature values of the user 199.

For example, when obtaining the first statistical standard corresponding to the stride length, the processor 114 may obtain the stride length of each group member, and then take the first 90% of the stride lengths of the group members as the first statistical standard of the stride length. In this case, when the stride length of the user 199 falls within the last 10% of the specific group, the processor 114 may then determine that the stride length of the user 199 does not satisfy the corresponding first statistical standard. For other step feature values and other walking limb feature values, the processor 114 may determine the corresponding first statistical standard based on a similar principle, the details of which will not be repeatedly described herein.

In an embodiment, the processor 114 may also determine the first statistical standard corresponding to each step feature value and each walking limb feature value based on previously measured historical step feature values and historical walking limb feature values of the user 199.

In an embodiment, the processor 114 may obtain the step feature values and the walking limb feature values of the user 199 measured in the previous test as the historical step feature values and the historical walking limb feature values of the user 199. After that, the processor 114 may determine the first statistical standard of each of the step feature values and each of the walking limb feature values of the user 199 based on a specific ratio of each of the historical step feature values and each of the historical walking limb feature values.

For example, when determining the first statistical standard of the stride length of the user 199, the processor 114 may obtain the previously measured stride length (hereinafter referred to as historical stride length) of the user 199, and take a specific ratio (e.g., 90%) of historical stride length as the first statistical standard of the stride length of the user 199. When the processor 114 determines that the stride length of the user 199 does not satisfy the corresponding first statistical standard (e.g., the stride length of the user 199 is less than 90% of the historical stride length), this means that the stride length of the user 199 has shown a certain extent of regression (e.g., regression by more than 10%), which may thus be used as a basis for determining that the gait of the user 199 is abnormal. For other step feature values and other walking limb feature values, the processor 114 may determine the corresponding first statistical standard based on a similar principle, the details of which will not be repeatedly described herein.

In different embodiments, the value of Y may be set by the designer depending on the needs. For example, in a case where Y is set to 1, the processor 114 may determine that the gait of the user 199 belongs to an abnormal gait when any one of the step feature values and the walking limb feature values of the user 199 does not satisfy the corresponding first statistical standard. Moreover, in a case where Y is set to 2, the processor 114 may determine that the gait of the user 199 belongs to an abnormal gait when any two of the step feature values and the walking limb feature values of the user 199 do not satisfy the corresponding first statistical standard. Nonetheless, the disclosure is not limited thereto.

In a fifth embodiment, the processor 114 may select an N number of specific values (e.g., first values) from the step feature values and the walking limb feature values of the user 199, and may map the specific values into a plurality of mapped values according to a K number of reference bases corresponding to each specific value, where N and K are positive integers, and each mapped value falls within a predetermined range.

After that, the processor 114 may perform a weighting operation on the mapped values to obtain a weighting operation result. Then, in response to determining that the weighting operation result does not satisfy a second statistical standard, the processor 114 may determine that the gait of the user 199 belongs to an abnormal gait, and in the opposite case, the processor 114 may determine that the gait of the user 199 belongs to a normal gait. Nonetheless, the disclosure is not limited thereto.

In an embodiment, for a first specific value in the specific values, the processor 114 may obtain a reference mean and a reference difference factor corresponding to the first specific value, accordingly estimate the reference bases corresponding to the first specific value.

In an embodiment, the reference mean may be represented as M, and the reference difference factor may be represented as S. In an embodiment, the reference bases corresponding to the first specific value may be represented as $M+iS$, where i is an integer, $i \in [-a, \ldots, +a]$, and a is a positive integer.

Figure 7:
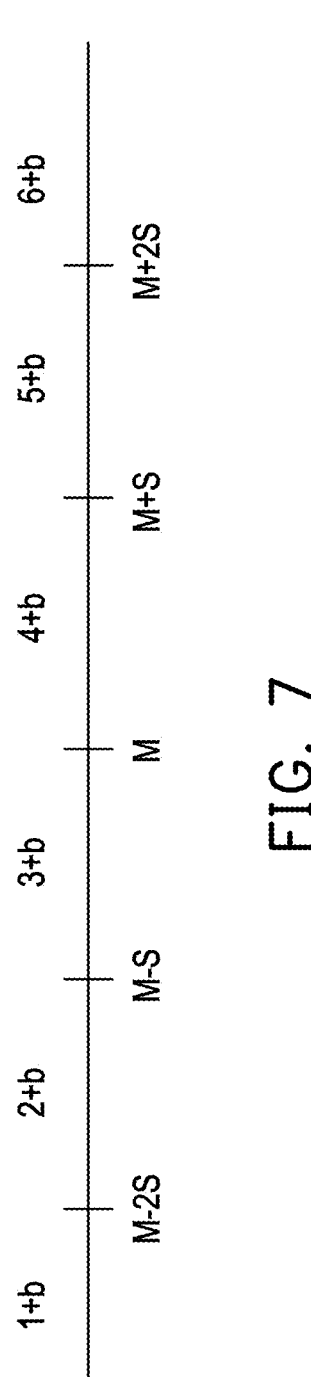
FIG. 7 is a schematic diagram illustrating a plurality of reference bases for determining a first specific value according to an embodiment of the invention.

With reference to FIG. 7, which is a schematic diagram illustrating a plurality of reference bases for determining a first specific value according to an embodiment of the invention. In FIG. 7, assuming that a is 2, then the reference bases may respectively be M−2S, M−S, M, M+S, and M+2S, but are not limited thereto.

Based on the architecture of FIG. 7, the processor 114 may map the first specific value into a first mapped value in the mapped values. In an embodiment, in response to determining that the first specific value is between the j-th reference basis and the j+1-th reference basis, the processor 114 may determine that the first mapped value is $j+1+b$, where $1 \leq j \leq K-1$, and b is a constant. In response to determining that the first specific value is less than the first reference basis (e.g., M−2S), the processor 114 may determine that the first mapped value is $1+b$. In response to determining that the first specific value is greater than the K-th reference basis (e.g., M+2S), the processor 114 may determine that the first mapped value is $K+1+b$.

For ease of description, it is assumed that b is 0 in the following, but the invention is not limited thereto. In this case, when the first specific value is less than the first reference basis (e.g., M−2S), the processor 114 may map the first specific value into 1. When the first specific value is between the first reference basis (i.e., M−2S) and the second reference basis (i.e., M−S), the processor 114 may map the first specific value into 2. When the first specific value is between the second reference basis (i.e., M−S) and the third reference basis (i.e., M), the processor 114 may map the first specific value into 3. When the first specific value is between the third reference basis (i.e., M) and the fourth reference basis (i.e., M+S), the processor 114 may map the first specific value into 4. When the first specific value is between the fourth reference basis (i.e., M+S) and the fifth reference basis (M+2S), the processor 114 may map the first specific value into 5. When the first specific value is greater than the fifth reference basis (e.g., M+2S), the processor 114 may map the first specific value into 6. Nonetheless, the disclosure is not limited thereto.

In the scenario of FIG. 7, it can be seen that the predetermined range of the first mapped value is, for example, 1+b, 2+b, 3+b, 4+b, 5+b, and 6+b. In other embodiments, for other specific values, the processor 114 may map each of the specific values into the corresponding mapped values based on the above teaching, and the mapped values may have the same predetermined range as that of the first mapped value. Nonetheless, the disclosure is not limited thereto. It should be noted that the embodiments of FIG. 2A to FIG. 7 may also be applied to the gait evaluating system 100B of FIG. 1B.

In different embodiments, the processor 114 in FIG. 1A and FIG. 1B may determine the reference mean (i.e., M) and the reference difference factor (i.e., S) of the first specific value based on different principles.

For example, assuming that the gait speed is the first specific value under consideration, then the processor 114 in FIG. 1A and FIG. 1B may obtain a mean of the general normal gait speed as the reference mean of the first specific value, and then take the specific ratio of the mean as the reference difference factor based on the relevant literature documents (e.g., "Bohannon R W, Williams Andrews A. Normal walking speed: a descriptive meta-analysis. Physiotherapy. 2011 September" or "Studenski S, Perera S, Patel K, Rosano C, Faulkner K, Inzitari M, Brach J, Chandler J, Cawthon P, Connor E B, Nevitt M, Visser M, Kritchevsky S, Badinelli S, Harris T, Newman A B, Cauley J, Ferrucci L, Guralnik J. Gait speed and survival in older adults. JAMA. 2011 Jan. 5"). For example, assuming that the specific ratio is 10%, then the reference bases corresponding to the gait speed may be, for example but not limited to, 80%, 90%, 100%, 110%, and 120% of M. For another example, assuming that the forward torso inclination angle is the first specific value under consideration, then the processor 114 in FIG. 1A and FIG. 1B may obtain a mean of the general normal forward torso inclination angle as the reference mean of the first specific value, and then take the specific ratio of the mean as the reference difference factor based on the relevant literature documents (e.g., "Gong H, Sun L, Yang R, Pang J, Chen B, Qi R, Gu X, Zhang Y, Zhang T M. Changes of upright body posture in the sagittal plane of men and women occurring with aging—a cross sectional study. BMC Geriatr. 2019 Mar. 5"). For example, assuming that the specific ratio is 10%, then the reference bases corresponding to the forward torso inclination angle may be, for example but not limited to, 80%, 90%, 100%, 110%, and 120% of M. For other first specific values, the processor 114 in FIG. 1A and FIG. 1B may determine the corresponding reference bases based on the above teaching, the details of which will not be repeatedly described herein.

In some embodiments, the processor 114 in FIG. 1A and FIG. 1B may also find a first reference value corresponding to the first specific value from the reference step feature values and the reference walking limb feature values of each group member in the specific group. After that, the processor 114 in FIG. 1A and FIG. 1B may then obtain a mean and a standard deviation of the first reference value of each group member, and define the mean and the standard deviation respectively as the reference mean (i.e., M) and the reference difference factor (i.e., S) of the first specific value.

For example, assuming that the first specific value is the stride length of the user 199, then the processor 114 in FIG. 1A and FIG. 1B may find the stride length of each group member as the first reference value of each group member, and accordingly estimate a mean and a standard deviation of the stride length of each group member. After that, the processor 114 in FIG. 1A and FIG. 1B may take the mean and the standard deviation as the reference mean (i.e., M)

and the reference difference factor (i.e., S) of the first specific value, and accordingly determine the reference bases corresponding to the stride length.

For another example, assuming that the first specific value is the gait speed of the user 199, then the processor 114 in FIG. 1A and FIG. 1B may find the gait speed of each group member as the first reference value of each group member, and accordingly estimate a mean and a standard deviation of the gait speed of each group member. After that, the processor 114 in FIG. 1A and FIG. 1B may take the mean and the standard deviation as the reference mean (i.e., M) and the reference difference factor (i.e., S) of the first specific value, and accordingly determine the reference bases corresponding to the gait speed.

After obtaining an N number of mapped values of the N number of specific values, the processor 114 in FIG. 1A and FIG. 1B may perform the weighting operation on the mapped values to generate the weighting operation result. In an embodiment, the respective weights of the N number of mapped values may be determined by the designer depending on the needs. For example, assuming that the N number of specific values are the gait speed and the torso inclination angle of the user 199, then after mapping the gait speed and the torso inclination angle of the user 199 into two corresponding mapped values, the processor 114 in FIG. 1A and FIG. 1B may obtain the corresponding weighting operation result based on formula "$P_1 \times W_1 + P_2 \times W_2$", where $P_1$ and $P_2$ are the mapped values respectively corresponding to the gait speed and the torso inclination angle, and $W_1$ and $W_2$ are weights (both of which may be 50%, for example) respectively corresponding to $P_1$ and $P_2$. Nonetheless, the disclosure is not limited thereto.

After that, the processor 114 in FIG. 1A and FIG. 1B may determine whether the weighting operation result satisfies the second statistical standard. In some embodiments, the processor 114 may determine the second statistical standard based on a mechanism below.

For example, the processor 114 in FIG. 1A and FIG. 1B may obtain an N number of reference values corresponding to the N number of specific values from the reference step feature values and the reference walking feature values of each group member of the specific group. Following the above example, assuming that the gait speed and the torso inclination angle of the user 199 are the N number of specific values under consideration, then the processor 114 may obtain the gait speed and the torso inclination angle of each group member as the N number of reference values of each group member.

After that, the processor 114 in FIG. 1A and FIG. 1B may map the N number of reference values of each group member into a plurality of reference mapped values according to the reference bases corresponding to each specific value, where each reference mapped value falls within the predetermined range. In an embodiment, the processor 114 in FIG. 1A and FIG. 1B may map the N number of reference values of each group member into the corresponding reference mapped values with reference to mapping the first specific value of the user 199 into the corresponding first mapped value. Therefore, the details will not be repeatedly described herein.

Then, the processor 114 in FIG. 1A and FIG. 1B may perform a weighting operation on the N number of reference mapped values of each group member to generate a reference weighting operation result of each group member. Following the above example, after mapping the gait speed and the torso inclination angle of a certain group member into two corresponding reference mapped values, the processor 114 in FIG. 1A and FIG. 1B may obtain the corresponding reference weighting operation result based on formula "$P'_1 \times W_1 + P'_2 \times W_2$", where $P'_1$ and $P'_2$ are the reference mapped values respectively corresponding to the gait speed and the torso inclination angle of the certain group member.

After that, the processor 114 in FIG. 1A and FIG. 1B may determine the second statistical standard based on the reference weighting operation result of each group member. In an embodiment, the processor 114 in FIG. 1A and FIG. 1B may, for example, take the last 90% of the reference weighting operation results of the group members as the second statistical standard. In this case, in response to determining that the weighting operation result of the user 199 falls within the last 90% of the reference weighting operation results of the group member, the processor 114 in FIG. 1A and FIG. 1B may determine that the weighting operation result of the user 199 satisfies the second statistical standard. On the other hand, in response to determine that the weighting operation result of the user 199 falls within the top 10% of the reference weighting operation results of the group member, the processor 114 in FIG. 1A and FIG. 1B may determine that the weighting operation result of the user 199 does not satisfy the second statistical standard. Nonetheless, the disclosure is not limited thereto.

In an embodiment, in the case where it is determined that the gait of the user 199 belongs to an abnormal gait, the processor 114 in FIG. 1A and FIG. 1B may further determine whether the gait of the user 199 belongs to a non-neuropathic gait or a neuropathic gait.

In an embodiment, the processor 114 in FIG. 1A and FIG. 1B may determine whether the stride-to-stride variation of the user 199 satisfies a third statistical standard. If so, the processor 114 in FIG. 1A and FIG. 1B may determine that the gait of the user 199 belongs to a neuropathic gait, and in the opposite case, the processor 114 in FIG. 1A and FIG. 1B may determine that the gait of user belongs to a non-neuropathic gait.

In an embodiment, the processor 114 in FIG. 1A and FIG. 1B may determine the third statistical standard based on the stride-to-stride variation of each group member in the specific group. For example, the processor 114 in FIG. 1A and FIG. 1B may take the first 70% of the stride-to-stride variations of the group members as the third statistical standard. In this case, in response to determining that the stride-to-stride variation of the user 199 falls within the top 70% of the stride-to-stride variations of the group members, the processor 114 in FIG. 1A and FIG. 1B may determine that the stride-to-stride variation of the user 199 satisfies the third statistical standard. On the other hand, in response to determining that the stride-to-stride variation of the user 199 falls within the last 30% of the stride-to-stride variations of the group members, the processor 114 in FIG. 1A and FIG. 1B may determine that the stride-to-stride variation of the user 199 does not satisfy the third statistical standard. Nonetheless, the disclosure is not limited thereto.

In summary of the foregoing, in the invention, after the step feature values and the walking limb feature values when the user walks are obtained through the pressure detection device and the limb sensing device, these feature values may be integrated for evaluating the gait of the user. Accordingly, in the invention, after the user takes a small amount of walk, the health condition of the user can be grasped accordingly, allowing relevant caregivers to take corresponding measures based on the health condition of the user, thereby achieving the effect of preventing the user from falls.

Although the invention has been disclosed in the above embodiments, they are not used to limit the invention. Any person having ordinary knowledge in the related technical field may make some changes and modifications without departing from the spirit and scope of the invention. Therefore, the protection scope of the invention shall be subject to the scope as defined in the appended claims.

What is claimed is:

1. A gait evaluating system, comprising:
   a pressure detection mat;
   at least one limb sensor;
   a display panel; and
   a processor, coupled to the pressure detection mat, the at least one limb sensor, and the display panel, wherein the processor is configured to:
   control the pressure detection mat to detect step pressure values corresponding to a plurality of steps of a user during a time period that the user walks on the pressure detection mat;
   control the at least one limb sensor to sense limb motions during the same time period that the user walks on the pressure detection mat;
   generate a plurality of step feature values of the user based on the step pressure values detected by the pressure detection mat;
   generate a plurality of walking limb feature values based on the limb motions sensed by the at least one limb sensor; and
   identify whether a gait type of the user belongs to a normal gait, a non-neuropathic gait or a neuropathic gait based on the step feature values and the walking limb feature values,
   wherein after identifying that the gait type of the user belongs to the non-neuropathic gait,
   the processor is configured to:
      control the display panel to display a first auxiliary information, wherein the first auxiliary information indicates a potential sarcopenia of the user;
      control the display panel to display a second auxiliary information, wherein the second auxiliary information indicates a dietary guideline for muscle building and for muscle strengthening; and
      control the display panel to display a third auxiliary information, wherein the third auxiliary information shows a motion instruction video for regaining or maintaining muscle strength of the user,
      wherein the first auxiliary information, the second auxiliary information, and the third auxiliary information facilitate the user to improve an abnormal gait resulting from the non-neuropathic gait.

2. The gait evaluating system according to claim 1, wherein the processor is further coupled to an audio player, wherein in response to identifying that the gait type of the user belongs to the neuropathic gait, the processor is configured to control the audio player to output a rhythmic audio, wherein the rhythmic audio is used for facilitating the user with an improved cadence and an improved gait speed.

3. The gait evaluating system according to claim 1, wherein in response to that the step feature values and the walking limb feature values of the user satisfies a first statistical standard, the processor is configured to identify that the gait type of the user belongs to a normal gait.

4. The gait evaluating system according to claim 1, wherein the processor is further configured to:
   select an N number of first values from the step feature values and the walking limb feature values;

map the N number of first values into a plurality of mapped values according to a K number of reference bases, wherein N and K are positive integers, and each of the mapped values falls within a predetermined range; and perform a weighting operation on the mapped values to generate a weighting operation result.

5. The gait evaluating system according to claim 4, wherein in response to that the weighting operation result does not satisfy a second statistical standard, the processor is configured to generate a stride-to-stride variation of the user based on the step pressure values detected by the pressure detection mat, wherein in response to that the stride-to-stride variation satisfies a third statistical standard, the processor is configured to identify that the gait of the user belongs to the neuropathic gait, in response to that the stride-to-stride variation does not satisfy the third statistical standard, the processor is configured to determine that the gait of the user belongs to the non-neuropathic gait.

6. The gait evaluating system according to claim 4, wherein a first group where the user belongs comprises a plurality of group members, and each of the group members has a plurality of reference step feature values and a plurality of reference walking limb feature values, and wherein the processor is configured to:

obtain a plurality of reference values corresponding to the N number of first values from the reference step feature values and the reference walking feature values of each of the group members;

map, according to the reference bases corresponding to each of the N number of first values, the reference values of each of the group members into a plurality of reference mapped values, wherein each of the reference mapped values falls within the predetermined range;

perform the weighting operation on the reference mapped values of each of the group members to generate a reference weighting operation result of each of the group members; and determine the second statistical standard based on the reference weighting operation result of each of the group members.

7. The gait evaluating system according to claim 4, wherein the N number of first values selected from the step feature values comprise a specific value, and the processor is configured to:

obtain a reference mean corresponding to the specific value;

obtain a reference difference factor corresponding to the specific value; and estimate the K number of reference bases corresponding to the specific value.

8. The gait evaluating system according to claim 5, wherein a first group where the user belongs comprises a plurality of group members, and each of the group members has the stride-to-stride variation, and the processor is configured to determine the third statistical standard based on the stride-to-stride variation of each of the group members.

9. The gait evaluating system according to claim 7, wherein a first group where the user belongs comprises a plurality of group members, and each of the group members has a plurality of reference step feature values and a plurality of reference walking limb feature values, and the processor is configured to:

find a first reference value corresponding to a second value from the reference step feature values and the reference walking limb feature values of each of the group members;

obtain a mean and a standard deviation of the first reference value of each of the group members; and respectively define the mean and the standard deviation as the reference mean and the reference difference factor of the second value.

10. The gait evaluating system according to claim 9, wherein the mapped values comprise a first mapped value corresponding to the second value, the reference mean is represented as M, the reference difference factor is represented as S, and the reference bases corresponding to the second value is represented as M+IS, where i is an integer, $i \in [-a, \ldots, +a]$, and a is a positive integer, and wherein:

in response to determining that the second value is between a j-th reference basis and a j+1-th reference basis in the reference bases, the processor is configured to determine that the first mapped value is j+1+b, where $1 \leq j \leq K-1$, and b is a constant;

in response to determining that the second value is less than a first reference basis in the reference bases, the processor is configured to determine that the first mapped value is 1+b; and in response to determining that the second value is greater than a K-th reference basis in the reference bases, the processor is configured to determine that the first mapped value is K+1+b.

11. The gait evaluating system according to claim 1, wherein the pressure detection mat includes a plurality of pressure detectors for detecting the step pressure values corresponding to the steps of the user.

12. The gait evaluating system according to claim 1, wherein based on the step pressure values, the processor is configured to obtain at least one of a step length, a gait speed, a stride length, a cadence, a step width, a gait cycle, a stance time, a swing time, a center of pressure, a moving trajectory, a double support time, a foot pressure distribution, and a stride-to-stride variation of the user as the step feature values.

13. The gait evaluating system according to claim 1, wherein based on the step pressure values, the processor is configured to obtain at least one of a get-up time, a turn time, a sit-down time, a walk speed, a walk time, and a total performance time of the user in a timed up and go test on the pressure detection mat as the step feature values.

14. The gait evaluating system according to claim 1, wherein the at least one limb sensor comprises a plurality of inertial sensors configured to be worn on the user, wherein the processor is configured to:

obtain, at a t-th time point, a plurality of three-dimensional spatial positions of the inertial sensors as the sensing data, and accordingly establishes a spatial distribution diagram of the inertial sensors at the t-th time point, wherein the spatial distribution diagram at the t-th time point comprises a plurality of reference points corresponding to the inertial sensors;

connect the reference points in the spatial distribution diagram into a skeleton diagram of the user at the t-th time point based on a relative position between a plurality of joints of the user, wherein the skeleton diagram comprises a plurality of joint angles at the t-th time point; and obtain a plurality of angle values of the joint angles, and takes the angle values as the walking limb feature values of the user at the t-th time point.

15. The gait evaluating system according to claim 1, wherein the at least one limb sensor comprises a first video camera and a second video camera having different imaging ranges, wherein the processor is configured to:

obtain, at a t-th time point, a first walking image captured by the first video camera when the user walks on the pressure detection device, and obtaining a first skeleton diagram in the first walking image;

obtain, at the t-th time point, a second walking image captured by the second video camera to the user on the pressure detection device, and obtains a second skeleton diagram in the second walking image, wherein the first skeleton diagram and the second skeleton diagram correspond to a first human body; and project, based on a relative position between the first video camera and the second video camera, the first skeleton diagram and the second skeleton diagram into a first integrated skeleton diagram, the first integrated skeleton diagram comprising a plurality of joint angles at the t-th time point, wherein the joint angles correspond to a plurality of joints of the first human body;

wherein in response to determining that the first integrated skeleton diagram satisfies a specified condition, the processor is configured to obtain a plurality of angle values of the joint angles, and takes the angle values as the walking limb feature values of the user at the t-th time point.

16. The gait evaluating system according to claim 15, wherein in response to determining that the first walking image and the second walking image do not respectively comprise a third skeleton diagram and a fourth skeleton diagram corresponding to a second human body, the processor is configured to determine that the first integrated skeleton diagram satisfies the specified condition.

17. The gait evaluating system according to claim 16, wherein in response to determining that the first walking image and the second walking image also respectively comprise the third skeleton diagram and the fourth skeleton diagram, the processor is configured to project the third skeleton diagram and the fourth skeleton diagram into a second integrated skeleton diagram based on the relative position between the first video camera and the second video camera;

wherein the processor is further configured to obtain a first projection error of the first integrated skeleton diagram and a second projection error of the second integrated skeleton diagram, in response to determining that the first projection error is less than the second projection error, the processor is configured to determine that the first integrated skeleton diagram satisfies the specified condition;

in response to determining that the first projection error is not less than the second projection error, the processor is configured to:

determine that the first integrated skeleton diagram does not satisfy the specified condition; and obtain the walking limb feature values of the user at the t-th time point based on the second integrated skeleton diagram.

18. The gait evaluating system according to claim 1, wherein the processor is further configured to:

obtain a plurality of historical step feature values and a plurality of historical walking limb feature values of the user, wherein the historical step feature values and the historical walking limb feature values correspond to the step feature values of the user and the walking limb feature values of the user; and determine, based on a first ratio of each of the historical step feature values and each of the historical walking limb feature values, the second statistical standard of each of the step feature values and each of the walking limb feature values.

* * * * *